(12) United States Patent
Tobin et al.

(10) Patent No.: US 9,579,357 B1
(45) Date of Patent: Feb. 28, 2017

(54) THERAPEUTIC COMPOSITIONS

(71) Applicants: William Tobin, Norwalk, CT (US); Peter Fratarcangelo, Norwalk, CT (US); Eugene Gresh, Ellington, CT (US); Rebecca Montrone, Keene, NH (US); Mauro Gozzo, Wallingford, CT (US)

(72) Inventors: William Tobin, Norwalk, CT (US); Peter Fratarcangelo, Norwalk, CT (US); Eugene Gresh, Ellington, CT (US); Rebecca Montrone, Keene, NH (US); Mauro Gozzo, Wallingford, CT (US)

(73) Assignee: ANC PRODUCTS, LLC, Norwalk, CT (US)

( * ) Notice: Subject to any disclaimer, the term of this patent is extended or adjusted under 35 U.S.C. 154(b) by 0 days.

(21) Appl. No.: 15/242,698

(22) Filed: Aug. 22, 2016

Related U.S. Application Data

(60) Provisional application No. 62/212,012, filed on Aug. 31, 2015.

(51) Int. Cl.

| | |
|---|---|
| *A61K 36/9066* | (2006.01) |
| *A61K 9/00* | (2006.01) |
| *A61K 36/28* | (2006.01) |
| *A61K 36/886* | (2006.01) |
| *A61K 47/46* | (2006.01) |
| *A61K 36/185* | (2006.01) |
| *A61K 36/324* | (2006.01) |
| *A61K 47/12* | (2006.01) |
| *A61K 47/14* | (2006.01) |
| *A61K 31/10* | (2006.01) |
| *A61K 35/57* | (2015.01) |
| *A61K 31/366* | (2006.01) |
| *A61K 47/10* | (2006.01) |
| *A61K 33/06* | (2006.01) |
| *A61K 36/534* | (2006.01) |
| *A61K 31/045* | (2006.01) |
| *A61K 36/539* | (2006.01) |
| *A61K 31/355* | (2006.01) |
| *A61K 47/36* | (2006.01) |
| *A61K 31/23* | (2006.01) |

(52) U.S. Cl.
CPC ......... *A61K 36/9066* (2013.01); *A61K 9/0014* (2013.01); *A61K 31/045* (2013.01); *A61K 31/10* (2013.01); *A61K 31/23* (2013.01); *A61K 31/355* (2013.01); *A61K 31/366* (2013.01); *A61K 33/06* (2013.01); *A61K 35/57* (2013.01); *A61K 36/185* (2013.01); *A61K 36/28* (2013.01); *A61K 36/324* (2013.01); *A61K 36/534* (2013.01); *A61K 36/539* (2013.01); *A61K 36/886* (2013.01); *A61K 47/10* (2013.01); *A61K 47/12* (2013.01); *A61K 47/14* (2013.01); *A61K 47/36* (2013.01); *A61K 47/46* (2013.01)

(58) Field of Classification Search
None
See application file for complete search history.

(56) References Cited

U.S. PATENT DOCUMENTS

| | | |
|---|---|---|
| 5,569,676 A | 10/1996 | Diehl |
| 6,103,246 A | 8/2000 | Tisdale et al. |
| 6,309,675 B1 | 10/2001 | Sobczak |
| 6,417,227 B1 | 7/2002 | Lord et al. |
| 6,756,064 B1 | 6/2004 | Carrol |

*Primary Examiner* — Susan Hoffman
(74) *Attorney, Agent, or Firm* — McCormick, Paulding & Huber LLP

(57) ABSTRACT

A therapeutic topical composition comprising achillea millefolium (yarrow) extract, aloe vera, arnica montana flowers, annatto seed extract, boswellia serrate extract, marigold flower extract, cetearyl olivate, cetyl myristoleate, sunflower seed oil, sorbitan olivate, turmeric root extract, methylsulfonylmethane (MSM), emu oil, devil's claw root extract, yerba mate leaf extract, magnesium sulfate, peppermint oil, menthol, skullcap root extract, vitamin E, and yucca root extract useful for treatment of localized pain, inflammation, and/or swelling, and methods for making and using the composition.

18 Claims, No Drawings

THERAPEUTIC COMPOSITIONS

CROSS REFERENCE TO RELATED APPLICATION

This application is a Non-Provisional Application, claiming the benefit of U.S. Provisional Patent Application No. 62/212,012, filed Aug. 31, 2015, which is hereby incorporated by reference in its entirety.

FIELD OF THE INVENTION

The present invention relates to therapeutic compositions useful in the topical treatment, prevention, or mitigation of pain, inflammation, and swelling as well as to methods for their use and manufacture.

BACKGROUND OF THE INVENTION

Physical activity such as strenuous exercise can subject the human body to intense strains, which may cause pain to result in the muscles and/or joints. In the case of a baseball pitcher, pain can be experienced in the arm or the shoulder. The shoulder pain often occurs in the same area. Although there are a number of available topical compositions for treatment of such pain, the efficacy of such compositions is less than optimal. There is a need for more effective topical compositions for treatment of muscle pain, particularly pain in the arms of baseball pitchers.

Exercise causes the muscles to use more oxygen. If the circulation to the muscle is partially or totally blocked, activities of the muscle such as raising or swinging the arm may cause muscle fatigue, pain, or aching. Recurring muscle pain (for example, in the arm) may be at least partially a result of the muscles not receiving enough oxygen and nutrients or poor removal of metabolic products of exercise (such as lactic acid) due to poor or inefficient circulation.

Furthermore, localized inflammation and swelling may result from an injury to the human body or arthritic pain in a joint may result from breaking down of the cartilage that covers the ends of the bones comprising the joint. Again, it is thought that increased circulation of the blood around the muscle and joint may have a beneficial effect on such inflammation and swelling and may facilitate the restoration of damaged tissue in such instances.

SUMMARY OF THE INVENTION

It is an object of the invention to provide topical compositions to treat injured and inflamed parts of the body having superior efficacy to compositions known in the art, as well as methods of making and using the compositions.

According to one aspect of the present invention, there is provided a topical therapeutic composition comprising: achillea millefolium (yarrow) extract, aloe vera, arnica montana flowers, annatto seed extract, boswellia serrate extract, marigold flower extract, cetearyl olivate, cetyl myristoleate, sunflower seed oil, sorbitan olivate, turmeric root extract, methylsulfonylmethane (MSM), emu oil, devil's claw root extract, yerba mate leaf extract, magnesium sulfate, peppermint oil, menthol, skullcap root extract, vitamin E, and yucca root extract.

The composition may further comprise beeswax, gluconolactone, glycerine, glyceryl stearate SE, caprylic/capric triglyceride, stearic acid, xanthan gum, and sodium benzoate as moisturizers, carriers, or preservatives.

DETAILED DESCRIPTION OF THE INVENTION

In accordance with the present invention, inflammation, pain, and swelling in a subject are effectively mitigated, prevented, or treated by topically administering to the afflicted subject a therapeutically effective amount of the therapeutic composition of the invention. For treatment of existing pain, inflammation, or swelling, the therapeutic composition is topically applied to the site of the existing pain, inflammation or swelling. For prevention or mitigation of anticipated inflammation, pain, or swelling due to expected physical activity, the therapeutic composition is applied topically to the site of the anticipated inflammation, pain, or swelling.

The composition of the invention comprises the following relative amounts of ingredients. The yarrow extract may be present in the composition in the range of from about 0.01% to about 0.04% by weight, preferably about 0.01-0.03% by weight. The aloe vera may be present in the composition in the range of from about 1% to about 30% by weight, preferably about 4-6% by weight. The arnica montana extract may be present in the composition in the range of from about 0.05% to about 0.8% by weight, preferably about 0.05-0.15% by weight. The beeswax may be present in the composition in the range of from about 0.5% to about 10% by weight, preferably about 0.5-2% by weight. The annatto seed extract may be present in the composition in the range of from about 0.01% to about 0.2% by weight, preferably about 0.01-0.1% by weight. The boswellia serrate extract may be present in the composition in the range of from about 0.05% to about 0.2% by weight, preferably about 0.05-0.15% by weight. The marigold flower extract may be present in the composition in the range of from about 0.05% to about 0.2% by weight, preferably about 0.05-0.15% by weight. The carpylic/capric triglyceride may be present in the composition in the range of from about 0.5% to about 2% by weight, preferably about 0.75-1.25% by weight. The cetearyl olivate may be present in the composition in the range of from about 1% to about 4% by weight, preferably about 1.5-2.5% by weight. The cetyl myristoleate may be present in the composition in the range of from about 0.01% to about 15% by weight, preferably about 0.01-0.03% by weight. The turmeric root extract may be present in the composition in the range of from about 0.05% to about 1.5% by weight, preferably about 0.07-0.12% by weight. The methylsulfonylmethane (MSM) may be present in the composition in the range of from about 1% to about 20% by weight, preferably about 2-4% by weight. The emu oil may be present in the composition in the range of from about 0.01% to about 20% by weight, preferably about 0.01-1.0% by weight. The gluconolactone may be present in the composition in the range of from about 0.3% to about 1.5% by weight, preferably about 0.4-0.9% by weight. The glycerin may be present in the composition in the range of from about 1% to about 8% by weight, preferably about 3-5% by weight. The glyceryl stearate SE may be present in the composition in the range of from about 1% to about 10% by weight, preferably about 4-6% by weight. The devil's claw root extract may be present in the composition in the range of from about 0.01% to about 0.8% by weight, preferably about 0.05-0.15% by weight. The sunflower seed oil may be present in the composition in the range of from about 0.1% to about 2% by weight, preferably about 0.3-0.7% by weight. The yerba mate leaf extract may be present in the composition in the range of from about 0.01% to about 0.2% by weight, preferably about 0.07-0.15% by weight. The magnesium sulfate may be present in the composition in the range of from about 1% to about 30% by weight, preferably about 2-4% by weight. The peppermint oil may be present in the composition in the range of from about 0.03% to about 3% by weight, preferably about 0.1-0.2% by weight. The menthol may be present in the composition in the range of from about 1.25% to about 10% by weight, preferably about 1.25% by weight. The skullcap root extract may be present in the composition in the range of from about 0.01% to about 0.2% by weight, preferably about 0.01-0.03% by weight. The sodium benzoate may be present in the composition in the range of from about 0.1% to about 0.6% by weight, preferably about 0.2-0.4% by weight. The sorbitan olivate may be present in the composition in the range of from about 0.5% to about 4% by weight, preferably about 1-3% by weight. The steric acid may be present in the composition in the range of from about 1% to about 6% by weight, preferably about 2-4% by weight. The vitamin E may be present in the composition in the range of from about 0.05% to about 2% by weight, preferably about 0.08-0.12% by weight. The xanthan gum may be present in the composition in the range of from about 0.1% to about 2.5% by weight, preferably about 0.2-0.8% by weight. The yucca root extract may be present in the composition in the range of from about 0.01% to about 0.4% by weight, preferably about 0.01-0.03% by weight. The composition also comprises water.

One preferred composition of the invention comprises 0.02 wt. % yarrow extract, 5 wt. % aloe vera, 0.1 wt % arnica montana extract, 1 wt. % beeswax, 0.01 wt. % annatto seed extract, 0.1 wt. % boswellia serrate extract, 0.1 wt. % marigold flower extract, 1 wt. % carpylic/capric triglyceride, 2 wt. % cetearyl olivate, 0.01 wt. % cetyl myristoleate, 0.1 wt. % turmeric root extract, 3 wt. % methylsulfonylmethane (MSM), 0.05 wt. % emu oil, 0.65 wt. % gluconolactone, 4 wt. % glycerin, 5 wt. % glyceryl stearate SE, 0.1 wt. % devil's claw root extract, 0.5 wt. % sunflower seed oil, 0.1 wt. % yerba mate leaf extract, 3 wt. % magnesium sulfate, 0.15 wt. % peppermint oil, 1.25 wt. % menthol, 0.02 wt. % skullcap root extract, 0.3 wt. % sodium benzoate, 2 wt. % sorbitan olivate, 3 wt. % steric acid, 0.1 wt. % vitamin E, 0.5 wt. % xanthan gum, and 0.02 wt. % yucca root extract, plus sufficient water to make 100%.

The present therapeutic compositions may further enhance the activity of other pharmaceuticals (such as topical analgesic and anti-inflammatory compounds and other natural ingredients such a glucosamine and condroitin) combined with them because of their deeper penetration into the dermis. The composition will effectively pull the added topical pharmaceutical into the lower layers of the skin and thereby result in more effective topical action, such as treatment of pain or inflammation. For example, by adding a topical therapeutic compound such as ibuprofen to the composition, the effectiveness of the ibuprofen will be increased by being drawn further into the skin. In this way, a lower level of ibuprofen in a composition of the invention may achieve the same effectiveness as a higher level of ibuprofen delivered in a conventional manner. Such a combination of a topical therapeutic with the subject composition would deliver a significant medical benefit because a patient could be treated with lower levels of drug and thereby have fewer adverse events or adverse events that are less severe.

The composition is preferably applied by applying it to the skin and massaging it in. The formulation may be a cream, gel, ointment, or lotion. A cream formulation is preferred for ease of application.

According to another aspect of the invention, there is provided a method of treating muscle or joint pain in a subject in need of such treatment, which comprises topically applying a composition of the invention to the site of the existing or anticipated muscle or joint pain. That is, the present therapeutic composition may be topically applied to the site of existing pain, such as that due to strenuous exercise or arthritis. Alternatively, the present therapeutic composition may be applied to an area (such arms or legs) which the subject expects to exercise strenuously in order to prevent or lessen the pain expected to result from that exercise. With respect to a baseball pitcher, the method comprises applying the therapeutic composition to the arm and shoulder area of the pitcher (as by rubbing it in) either prior to or after a throwing session, or both.

According to another aspect of the present invention, there is provided a method of preparing a therapeutic composition comprising the steps of: 1) preparing an aqueous mixture of aloe vera, the botanical extracts, glycerin, and magnesium sulfate with heating to about 165° C.; 2) preparing a mixture of sunflower oil, emu oil, caprylic/capric triglyceride, vitamin E, cetyl myristoleate, beeswax, and stearic acid with heating to about 165° C.; 3) slowly adding the oil phase to the aqueous phase with agitation; 4) adding cetearyl olivate, sorbitan olivate, glyceryl stearate, and xanthan gum with mixing and allow to cool to about 110° C.; 5) adding gluconolactone, sodium benzoate, peppermint oil and menthol; 6) mixing until homogeneous. The amounts of ingredients used in the method are within the ranges described above. The method may further comprise the step of adding a pharmaceutical drug at any of the above steps as noted above. By altering the quantity of carrier ingredients, the formulation may also be made as a gel, ointment, or lotion, as may be desired. Although the above method is the preferred way of making the therapeutic compositions, those of skill in the art will readily appreciate that other combinations of steps may be used to achieve the same result.

The ingredients of the therapeutic composition of the present invention are summarized in Table 1 below with respect to a description thereof, the active ingredients therein, percentages by weight range for each active ingredient, and the benefits thereof.

TABLE 1

| Ingredient | Minimum Range % | Current % (w/w) | Maximum Range % | Description | Contains | Benefit |
| --- | --- | --- | --- | --- | --- | --- |
| ACHILLEA MILLEFOLIUM (Yarrow) EXTRACT | 0.01 | 0.02 | 0.40 | Achille millefolium, known commonly as yarrow common yarrow, is a flowering plant in the family Asteraceae. It is native to temperate regions of the Northern Hemisphere in Asia, Europe, and North America. The plant also has a long history as a powerful 'healing herb' used topically for wounds, cuts and abrasions. | Sesquiterpene lactones, polyacetylenes, simple coumarins, and flavonoids. | Lower fevers, induces sweating, stops cramps, relieves inflammation, and stimulates the release of |

TABLE 1-continued

| Ingredient | Minimum Range % | Current % (w/w) | Maximum Range % | Description | Contains | Benefit |
|---|---|---|---|---|---|---|
| | | | | | | stomach acid to digest proteins and fats. |
| ALOE BARBADENSIS (Aloe Vera Gel) JUICE | 1.00 | 5.00 | 30.00 | Aloe vera, otherwise known as barbados aloe vera and curacao aloe vera, is a perennial plant found wild in East and South Africa. It is also cultivated in the West Indies and other tropical areas. The strong, fibrous root produces a rosette of fleshy basal leaves as in the agave, but considerably smaller. The narrow-lanceolate leaves are 1 to 2 feet long and whitish-green on both sides, and they bear spiny teeth on the margins. | Carrisyn, salicylates, enzyme that inhibits bradykinin (pain transmitter), magnesium lactate, compounds that exhibit bacteriostatic and antifungal activity. | Anti-inflammatory and also helps conduct the active ingredient of the herbs through the skin barrier. |
| ARNICA MONTANA (Arnica) EXTRACT | 0.05 | 0.10 | 0.80 | Arnica montana is a perennial flowering plant native to southern Russia and other mountainous areas in Europe. In Germany, it is a protected species. Vernacular names include leopard's bane and mountain tobacco. | Sesquiterpene lactones that inhibit collagen-induced platelet aggregation and thromboxane formation. | Has an analgesic, anticoagulation, and anti-inflammatory effect. |
| BEESWAX | 0.50 | 1.00 | 10.00 | Beeswax is a natural wax produced in the bee hive of honey bees of the genus Apis. Chemically, beeswax consists of mainly esters of fatty acids and various long-chain alcohols. | None | Thickener to strengthen and preserve cream. |
| BIXA ORELLANA (Annatto) SEED EXTRACT | 0.01 | 0.01 | 0.20 | It is easily incorporated into creams, sunscreen, and lip balms where it helps to condition hair and protect against ultraviolet rays. It also has been used as diuretic, laxative, antibilious, antiemetic, and astringent agents, as a blood purifier, in jaundice, in dysentery, and externally as scar-preventive. | Tocotrienols, beta-carotene, essential oil, saturated and unsaturated fatty acids, flavonoids and vitamin C | UV protectant, used as a diuretic, astringent and assists in tissue repair |
| BOSWELLIA SERRATA EXTRACT | 0.05 | 0.10 | 0.20 | Boswellia extract has been used for centuries to treat a wide range of ailments, including arthritis, diarrhea, dysentery, lung disease and worms, Boswellia extract is best known among herbalists as a treatment for arthritis. One of its primary active ingredients, boswellic acid, is an anti-inflammatory that can be used in ointments to ease joint pain. | Boswellic acid | Treatment for arthritis and as such used as an anti-inflammatory agent |
| CALENDULA OFFICINALIS (Marigold) FLOWER EXTRACT | 0.05 | 0.10 | 0.20 | Calendula officinalis (pot marigold, ruddles, common marigold, garden marigold, English marigold, or Scottish marigold) is a plant in the genus Calendula of the family Asteraceae. It is probably native to southern Europe, though its long history of cultivation makes its precise origin unknown, and it may possibly be of garden origin. It is also widely naturalized in north to southern England and elsewhere in warm temperate regions of the world. Calendula officianalis is a short-lived aromatic herbaceous perennial, growing to 80 cm (31 in) tall, with sparsely branched lax or erect stems. | Triterpenoids, flavonoids, and saponin fractions isolated from the flower include oleanolic acid and ursolic acid. | Has anti-inflammatory, immuno-stimulating, antibacterial, antiviral, antiprotozoal, and antineoplastic properties. |
| CAPRY-LIC/CAPRIC TRIGLYC-ERIDE | 0.50 | 1.00 | 2.00 | It is considered an excellent emollient and skin-repairing ingredient due to its mix of fatty acids that skin can utilize to repair its surface and resist moisture loss. Caprylic/capric triglyceride can also function as a thickener, but its chief job is to moisturize and replenish skin. | Coconut oil and glycerin | Emollient, skin repair, can function as a thickener, moisturizes and replenishes skin. |
| CETEARYL OLIVATE | 1.00 | 2.00 | 4.00 | Cetearyl Olivate is a natural PEG-free emulsifiers from Olive oil. It reduces skin water loss, have high moisturizing effect, hypoallergenic and biomimics the skin. | Olive oil by esterification of its fatty acid groups and combined with sorbitol and ceteary lalcohol | Facilitates the retention of skin moisture and increases the active ingredient's resistance to water and/or sweat. |
| CETYL MYRISTO-LEATE | 0.01 | 0.01 | 15.00 | Cetyl myristoleate is a chemical compound which is a type of fatty acid ester or, more specifically, a cetylated fatty acid (CFA). It is the cetyl ester of myristoleic acid. | Cetyl ester. | Lubricates the joints and muscles, rebuilds cartilage, and is an immune system modulator. |

TABLE 1-continued

| Ingredient | Minimum Range % | Current % (w/w) | Maximum Range % | Description | Contains | Benefit |
|---|---|---|---|---|---|---|
| | | | | | | Also useful in relieving joint discomfort following exercise. |
| *CURCUMA LONGA* (Turmeric) EXTRACT | 0.05 | 0.10 | 1.50 | Turmeric (*Curcuma longa*) is a *rhizomatous herbaceous* perennial plant of the ginger family, *Zingiberaceae*. It is native in southeast India, and needs temperatures between 20° C. and 30° C. (68° F. and 86° F.) and a considerable amount of annual rainfall to thrive. | Curcuminoids and Volatile Oils. | Highly anti-inflammatory, analgesic, and contains antioxidant properties. |
| DIMETHYL SULFONE (MSM) | 1.00 | 3.00 | 20.00 | Methylsulfonylmethane (MSM) is an organosulfur compound. It is also known by several other names including DMSO2, methyl sulfone, and dimethyl sulfone. This colorless solid features the sulfonyl functional group and is considered relatively inert chemically. It occurs naturally in some primitive plants, is present in small amounts in many foods and beverages, and is marketed as a dietary supplement. | Dimethyl Sulfone | Helps deliver sulfur to the body to maintain connective tissue structure as well as reduce pain and provide anti-inflammatory effects. |
| EMU OIL | 0.01 | 0.05 | 20.00 | Emu oil is oil derived from adipose tissue harvested from certain subspecies of the emu, Dromaius novaehollandiae, a flightless bird indigenous to Australia. Unadulterated emu oil can vary widely in color and viscosity anywhere from an off-white creamy texture to a thin yellow liquid, depending on the diet of the emu and the refining method(s) used. It is composed of approximately 70% unsaturated fatty acids. | Essential Fatty acids: Omega-3, Omega-6, and Omega-9 (Oleic acid) | A natural pain relieving, anti-inflammatory, moisturizing oil with a pH balance very close to human skin. |
| GLUCONOLAC TONE | 0.30 | 0.65 | 1.50 | Gluconolactone is often added to formulas because of its skin-conditioning properties. The molecules that come together to form gluconolactone are naturally attracted to water. When the ingredient is applied to the skin, these "water hungry" molecules pull moisture out of the air and allow it to be absorbed by the skin. By drawing water droplets from the air in this way, gluconolactone helps to soften and soothe dry skin and replenish lost moisture. In addition, gluconolactone forms a barrier on the skin, preventing moisture already present in the tissue from evaporating. As a result, the substance is often used as an active ingredient in moisturizers, hair conditioners, body lotions and body butters. | Gluconic Acid | Moisturizer and antioxidant activity. |
| GLYCERIN | 1.00 | 4.00 | 8.00 | Also called glycerol or glycerine; it is present in all natural lipids (fats), whether animal or vegetable. It can be derived from natural substances by hydrolysis of fats and by fermentation of sugars. It can also be synthetically manufactured. Whether natural or synthetic, glycerin is a humectant and extremely hygroscopic, meaning it readily absorbs water from other sources. | Polyol (Sugar Alcohol) | Prevents dryness or scaling. |
| GLYCERYL STEREATE SE | 1.00 | 5.00 | 10.00 | Glyceryl Stearate and Glyceryl Stearate SE are esterification products of glycerin and stearic acid. Glyceryl Stearate is a white or cream-colored wax-like solid. Glyceryl Stearate SE is a "Self-Emulsifying" form of Glyceryl Stearate that also contains a small amount of sodium and or potassium stearate. | Glycerin and stearic acid | Acts as a lubricant on the skin's surface and also slows the loss of water from the skin by forming a barrier on the skin's surface. |
| *HARPA-GOPHYTUM PROCUMBENS* (Devil's Claw) ROOT EXTRACT | 0.01 | 0.10 | 0.80 | *Harpagophytum*, also called grapple plant, wood spider and most commonly devil's claw, is a genus of plants in the sesame family, native to southern Africa. It owes its common name Devil's Claw to the peculiar appearance of its hooked fruit. The plant's large tuberous roots are used medicinally to reduce pain and fever, and to stimulate digestion. European colonists brought devil's claw home where it was used to treat arthritis. *Harpagophytum procumbens* is mainly found in the eastern and south eastern parts of Namibia, | Harpogoside and Beta-sitosterol (anti-inflammatory properties). | Historically, it has been used to treat arthritis by decreasing inflammation, swelling and resulting pain. |

TABLE 1-continued

| Ingredient | Minimum Range % | Current % (w/w) | Maximum Range % | Description | Contains | Benefit |
|---|---|---|---|---|---|---|
| HELIANTHUS ANNUUS (Sunflower) SEED OIL | 0.10 | 0.50 | 2.00 | Southern Botswana and the Kalahari region of the Northern Cape, South Africa. Sunflower oil is a monounsaturated (MUFA)/polyunsaturated (PUFA) mixture of mostly oleic acid (omega-9)-linoleic acid (omega-6) group of oils. Sunflower oil is high in the essential vitamin E and low in saturated fat. | Palmitic acid (saturated): 5%, Stearic acid (saturated): 6%, Oleic acid (monounsaturated omega-9): 30%, Linoleic acid (polyunsaturated omega-6): 59% | Has smoothing properties and is considered noncomedogenic |
| ILEX PARA-GUARIENSIS (Yerba Mate) LEAF EXTRACT | 0.01 | 0.10 | 0.20 | Yerba mate is made from the naturally caffeinated and nourishing leaves of the celebrated South American rainforest holly tree (Ilex paraguariensis). Of the six commonly used stimulants in the world: coffee, tea, kola nut, cocoa and guarana, yerba mate triumphs as the most balanced, delivering both energy and nutrition. | 24 vitamins and minerals, 15 amino acids, antioxidants, plus stimulants - caffeine, theophylline, and theobromine | Yerba Mate is used as a stimulant to relieve mental and physical tiredness (fatigue) and to relieve joint pain. |
| MAGNESIUM SULFATE | 1.00 | 3.00 | 30.00 | Magnesium, as a pharmaceutical preparation, is used to treat conditions including magnesium deficiency and hypomagnesemia, as well as eclampsia. Usually in lower dosages, magnesium is commonly included in dietary mineral preparations, including many multivitamin preparations. | Magnesium sulfate | A natural muscle relaxant also vital for the normal conduction of electricity cell-to-cell. |
| MENTHA PIPERITA (Peppermint) OIL | 0.03 | 0.15 | 3.00 | Peppermint (Mentha piperita) also known as M. balsamea is a hybrid mint, a cross between watermint and spearmint. The plant, indigenous to Europe and the Middle East, is now widespread in cultivation in many regions of the world. It is found wild occasionally with its parent species. | Menthol, menthone, menthyl acetate, 1,8-cineole, limonene, beta-pinene and beta-caryophyllene. | Used for muscle and nerve-related pains as well as contributing to bringing ingredients through the epidermis layers and into deeper tissues. |
| MENTHOL | 1.25 | 1.25 | 10.00 | Menthol is an organic compound obtained from corn mint, peppermint or other mint oils. Menthol has local anesthetic and counterirritant qualities. Menthol's ability to chemically trigger the cold-sensitive TRPM8 receptors in the skin is responsible for the well-known cooling sensation it provokes when inhaled, eaten, or applied to the skin. Menthol's analgesic properties are mediated through a selective activation of x-opioid receptors. Menthol also blocks voltage-sensitive sodium channels, reducing neural activity that may stimulate muscles. | Menthol | FDA active ingredient as a topical analgesic. It is used to relieve minor aches and pains, such as muscle cramps, sprains, headaches and similar conditions |
| SCUTELLARIA BAICALENSIS (Baikal Skullcap) ROOT EXTRACT | 0.01 | 0.02 | 0.20 | Baikal skullcap is a plant. The root is used to make medicine. Common substitutions for Baikal skullcap in Chinese medicine include related plants whose scientific names are Scutellaria viscidula, Scutellaria amonea, and Scutellaria ikoninikovii. Baikal skullcap is used to treat respiratory infections, hay fever, and fever. It is also used for gastrointestinal (GI) infections, as well as liver problems including viralhepatitis and jaundice. | Baicalin | Reduce inflammation |
| SODIUM BENZOATE | 0.10 | 0.30 | 0.60 | Sodium benzoate is the sodium salt of Benzoic Acid. It is used as an antifungal preservative in pharmaceutical preparations and foods. It may also be used as a test for liver function. | Benzoic acid | Antifungal preservative |
| SORBITAN OLIVATE | 0.50 | 2.00 | 4.00 | Sorbitan Olivate is a natural PEG-free emulsifiers from Olive oil. It reduces skin water loss, have high moisturizing effect, hypoallergenic and biomimics the skin. | Olive oil by esterification of its fatty acid groups and combined with sorbitol and cetearyl alcohol | Facilitates the retention of skin moisture and increases the active ingredient's resistance to water and/or sweat. |

TABLE 1-continued

| Ingredient | Minimum Range % | Current % (w/w) | Maximum Range % | Description | Contains | Benefit |
|---|---|---|---|---|---|---|
| STEARIC ACID | 1.00 | 3.00 | 6.00 | Stearic Acid is a saturated long-chain fatty acid with an 18-carbon backbone. Stearic acid is found in various animal and plant fats, and is a major component of cocoa butter and shea butter. | Salts and esters | Lubrication |
| TOCOPHERYL ACETATE (Vitamin E) | 0.05 | 0.10 | 2.00 | Tocopheryl acetate, also known as vitamin E acetate, is a common vitamin supplement. It is the ester of acetic acid and tocopherol (vitamin E). It is often used in dermatological products such as skin creams. Tocopheryl acetate is not oxidized and can penetrate through the skin to the living cells. | Ester of acetic acid and tocopherol (vitamin E) | Increases energy, reduces muscle damage after exercise, and improves physical endurance and muscle strength. |
| XANTHAN GUM | 0.10 | 0.50 | 2.50 | Xanthan gum is a polysaccharide secreted by the bacterium Xanthomonas campestris, used as a food additive and rheology modifier, commonly used as a food thickening agent and a stabilizer to prevent ingredients from separating. | None | Thickening agent and stabilizer. |
| YUCCA EXTRACT | 0.01 | 0.02 | 0.40 | Yucca root comes from the flowering yucca plant which is a member of the lily family that can grow to heights of 40 feet or more. | Steroid-like saponins that elevate the body's production of cortisone. | It acts an anti-inflammatory. |

Example 1

Composition 1

A therapeutic composition is prepared as described above using the following proportions of ingredients: 0.02 wt. % yarrow extract, 5 wt. % aloe vera, 0.1 wt % arnica montana extract, 1 wt. % beeswax, 0.01 wt. % annatto seed extract, 0.1 wt. % boswellia serrate extract, 0.1 wt. % marigold flower extract, 1 wt. % carpylic/capric triglyceride, 2 wt. % cetearyl olivate, 0.01 wt. % cetyl myristoleate, 0.1 wt. % turmeric root extract, 3 wt. % methylsulfonylmethane (MSM), 0.05 wt. % emu oil, 0.65 wt. % gluconolactone, 4 wt. % glycerin, 5 wt. % glyceryl stearate SE, 0.1 wt. % devil's claw root extract, 0.5 wt. % sunflower seed oil, 0.1 wt. % yerba mate leaf extract, 3 wt. % magnesium sulfate, 0.15 wt. % peppermint oil, 1.25 wt. % menthol, 0.02 wt. % skullcap root extract, 0.3 wt. % sodium benzoate, 2 wt. % sorbitan olivate, 3 wt. % steric acid, 0.1 wt. % vitamin E, 0.5 wt. % xanthan gum, 0.02 wt. % yucca root extract and water q.s. The composition is effective to treat localized pain, inflammation and/or swelling when applied topically.

Example 2

Evaluation of Composition 1 in Baseball Pitchers

A controlled clinical study was performed on 4 male baseball players between the ages of 12-15. Subjects were crossed-over between a no treatment study session and a treatment study session. Each study session consisted of pre-session arm pain score assessment prior to any activity to ensure no subject injuries. All pain score readings ranged from 0-9, with 0 meaning no pain to 9 meaning extremely painful. A standard baseball warm up activity was completed, consisting of general throwing and stretching warm-up. Subjects then took a pulse oximetry reading of their index finger followed by a throwing session of 5 warm up pitches (standard 60 ft baseball pitching distance) at approximately 50% power. A series of 15 fastballs were then thrown at the subject's maximum attempted velocity. Speed was captured via a station manager with a standard radar gun. Accuracy (ball or strike) was also recorded by a second station manager. At the completion of the 15 fastball pitches, a pulse oximetry reading was taken. The subject then rested for an approximate 5-10 minute period, following which he repeated the throwing session until 2 full sessions were completed (30 total fastballs recorded).

The entire group of subjects completed the session as described above for both the no treatment group and treatment group. For the treatment group the treatment composition was applied to the throwing arm prior to standard baseball warm up activity. The treatment composition was applied liberally to the arm and shoulder region of the subject's throwing arm and massaged into the area until absorbed (approximately 30 seconds). There were no subject complaints or adverse events from applying the treatment formula through the end of the treatment assessment period.

The treatment group exhibited an overall 0.03 oxygen saturation unit increase in the average pulse oximetry reading as compared to no treatment. This result, although a very small increase, may suggest the formula has a unique ability to improve blood flow over a period of muscle exertion. An improved average pulse oximetry score for the treatment group suggests a comparative reduction in swelling when compared to no treatment as more blood oxygen is found in the extremities. Subject's average full session velocity over the entire study group was increased by 1.2 mph and strike accuracy improved from 43% to 54% in the treatment group versus no treatment. These results suggest that the composition of the invention may exhibit a unique ability to improve flexibility and stamina in subjects, thereby improving throwing velocity and accuracy.

Although not statistically powered to prove treatment formula efficacy, results suggest a positive trend in the efficacy of the treatment composition to aid in the decrease of muscle pain and swelling. Results suggest that the compositions of the invention have a unique ability to aid in reduction of pain and swelling in any situation where these conditions are exhibited.

Example 3

Other Evaluations of the Composition

Case 1 is a 72 year old female with arthritic pain in her shoulder. Subject had complained of intense shoulder pain upon waking due to a documented history of arthritis. Subject was given the treatment composition to apply at bedtime to the affected shoulder region. Each morning after application of the treatment composition, the subject has reported no shoulder pain upon wakening. Without application of the treatment composition, shoulder pain upon wakening has returned.

Case 2 is a 42 year old male with general aches and pains following strenuous exercise. Subject reported severe pain and swelling of the ankle, calf and knee region within 12 hours following strenuous exercise. Subject applied the treatment composition to these regions after strenuous exercise and reported no pain or swelling in these regions through 24 hours post exercise. Subject discontinued use of the treatment composition and has reported resumed pain and swelling to these regions within 12 hours following similar strenuous exercise.

In the description and claims of this specification the word "comprise" and variations of that word, such as "comprises" and "comprising" are not intended to exclude other features, additives, components, integers or steps but rather, unless otherwise stated explicitly, the scope of these words should be construed broadly such that they have an inclusive meaning rather than an exclusive one.

Although the therapeutic compositions of the invention have been described in the present disclosure by way of illustrative examples, it is to be understood that the invention is not limited thereto and that variations can be made as known by those skilled in the art without departing from the teachings of the invention defined by the appended claims.

What is claimed is:

1. A topical therapeutic composition which comprises 0.01-0.04 wt. % yarrow extract, 1-30 wt. % aloe vera, 0.05-0.8 wt % arnica montana extract, 0.5-10 wt. % beeswax, 0.01-0.2 wt. % annatto seed extract, 0.05-0.2 wt. % boswellia serrata extract, 0.05-0.2 wt. % marigold flower extract, 0.5-2 wt. % caprylic/capric triglyceride, 1-4 wt. % cetearyl olivate, 0.01-15 wt. % cetyl myristoleate, 0.05-1.5 wt. % turmeric root extract, 1-20 wt. % methylsulfonylmethane (MSM), 0.01-20 wt. % emu oil, 0.3-1.5 wt. % gluconolactone, 1-8 wt. % glycerin, 1-10 wt. % glyceryl stearate SE, 0.01-0.8 wt. % devil's claw root extract, 0.1-2 wt. % sunflower seed oil, 0.01-0.2 wt. % yerba mate leaf extract, 1-30 wt. % magnesium sulfate, 0.03-3 wt. % peppermint oil, 1.25-10 wt. % menthol, 0.01-0.2 wt. % skullcap root extract, 0.1-0.6 wt. % sodium benzoate, 0.5-4 wt. % sorbitan olivate, 1-6 wt. % stearic acid, 0.05-2 wt. % vitamin E, 0.1-2.5 wt. % xanthan gum, and 0.01-0.4 wt. % yucca root extract.

2. The composition of claim 1 which comprises 0.01-0.03 wt. % yarrow extract, 4-6 wt. % aloe vera, 0.05-0.15 wt % arnica montana extract, 0.5-2 wt. % beeswax, 0.01-0.1 wt. % annatto seed extract, 0.05-0.15 wt. % boswellia serrata extract, 0.05-0.15 wt. % marigold flower extract, 0.75-1.25 wt. % caprylic/capric triglyceride, 1.5-2.5 wt. % cetearyl olivate, 0.01-0.03 wt. % cetyl myristoleate, 0.07-0.12 wt. % turmeric root extract, 2-4 wt. % methylsulfonylmethane (MSM), 0.01-0.1 wt. % emu oil, 0.4-0.9 wt. % gluconolactone, 3-5 wt. % glycerin, 4-6 wt. % glyceryl stearate SE, 0.05-0.15 wt. % devil's claw root extract, 0.3-0.7 wt. % sunflower seed oil, 0.07-0.15 wt. % yerba mate leaf extract, 2-4 wt. % magnesium sulfate, 0.1-0.2 wt. % peppermint oil, 1.25 wt. % menthol, 0.01-0.03 wt. % skullcap root extract, 0.2-0.4 wt. % sodium benzoate, 1-3 wt. % sorbitan olivate, 2-4 wt. % stearic acid, 0.08-0.12 wt. % vitamin E, 0.2-0.8 wt. % xanthan gum, and 0.01-0.03 wt. % yucca root extract.

3. The composition of claim 1 which comprises 0.02 wt. % yarrow extract, 5 wt. % aloe vera, 0.1 wt % arnica montana extract, 1 wt. % beeswax, 0.01 wt. % annatto seed extract, 0.1 wt. % boswellia serrata extract, 0.1 wt. % marigold flower extract, 1 wt. % caprylic/capric triglyceride, 2 wt. % cetearyl olivate, 0.01 wt. % cetyl myristoleate, 0.1 wt. % turmeric root extract, 3 wt. % methylsulfonylmethane (MSM), 0.05 wt. % emu oil, 0.65 wt. % gluconolactone, 4 wt. % glycerin, 5 wt. % glyceryl stearate SE, 0.1 wt. % devil's claw root extract, 0.5 wt. % sunflower seed oil, 0.1 wt. % yerba mate leaf extract, 3 wt. % magnesium sulfate, 0.15 wt. % peppermint oil, 1.25 wt. % menthol, 0.02 wt. % skullcap root extract, 0.3 wt. % sodium benzoate, 2 wt. % sorbitan olivate, 3 wt. % stearic acid, 0.1 wt. % vitamin E, 0.5 wt. % xanthan gum, and 0.02 wt. % yucca root extract.

4. The composition of claim 1 which consists of 0.01-0.04 wt. % yarrow extract, 1-30 wt. % aloe vera, 0.05-0.8 wt % arnica montana extract, 0.5-10 wt. % beeswax, 0.01-0.2 wt. % annatto seed extract, 0.05-0.2 wt. % boswellia serrata extract, 0.05-0.2 wt. % marigold flower extract, 0.5-2 wt. % caprylic/capric triglyceride, 1-4 wt. % cetearyl olivate, 0.01-15 wt. % cetyl myristoleate, 0.05-1.5 wt. % turmeric root extract, 1-20 wt. % methylsulfonylmethane (MSM), 0.01-20 wt. % emu oil, 0.3-1.5 wt. % gluconolactone, 1-8 wt. % glycerin, 1-10 wt. % glyceryl stearate SE, 0.01-0.8 wt. % devil's claw root extract, 0.1-2 wt. % sunflower seed oil, 0.01-0.2 wt. % yerba mate leaf extract, 1-30 wt. % magnesium sulfate, 0.03-3 wt. % peppermint oil, 1.25-10 wt. % menthol, 0.01-0.2 wt. % skullcap root extract, 0.1-0.6 wt. % sodium benzoate, 0.5-4 wt. % sorbitan olivate, 1-6 wt. % stearic acid, 0.05-2 wt. % vitamin E, 0.1-2.5 wt. % xanthan gum, 0.01-0.4 wt. % yucca root extract, and water to make 100%.

5. The composition of claim 2 which consists of 0.01-0.03 wt. % yarrow extract, 4-6 wt. % aloe vera, 0.05-0.15 wt % arnica montana extract, 0.5-2 wt. % beeswax, 0.01-0.1 wt. % annatto seed extract, 0.05-0.15 wt. % boswellia serrata extract, 0.05-0.15 wt. % marigold flower extract, 0.75-1.25 wt. % caprylic/capric triglyceride, 1.5-2.5 wt. % cetearyl olivate, 0.01-0.03 wt. % cetyl myristoleate, 0.07-0.12 wt. % turmeric root extract, 2-4 wt. % methylsulfonylmethane (MSM), 0.01-0.1 wt. % emu oil, 0.4-0.9 wt. % gluconolactone, 3-5 wt. % glycerin, 4-6 wt. % glyceryl stearate SE, 0.05-0.15 wt. % devil's claw root extract, 0.3-0.7 wt. % sunflower seed oil, 0.07-0.15 wt. % yerba mate leaf extract, 2-4 wt. % magnesium sulfate, 0.1-0.2 wt. % peppermint oil, 1.25 wt. % menthol, 0.01-0.03 wt. % skullcap root extract, 0.2-0.4 wt. % sodium benzoate, 1-3 wt. % sorbitan olivate, 2-4 wt. % stearic acid, 0.08-0.12 wt. % vitamin E, 0.2-0.8 wt. % xanthan gum, 0.01-0.03 wt. % yucca root extract, and water to make 100%.

6. The composition of claim 3 which consists of 0.02 wt. % yarrow extract, 5 wt. % aloe vera, 0.1 wt % arnica montana extract, 1 wt. % beeswax, 0.01 wt. % annatto seed extract, 0.1 wt. % boswellia serrata extract, 0.1 wt. % marigold flower extract, 1 wt. % caprylic/capric triglyceride, 2 wt. % cetearyl olivate, 0.01 wt. % cetyl myristoleate, 0.1 wt. % turmeric root extract, 3 wt. % methylsulfonylmethane (MSM), 0.05 wt. % emu oil, 0.65 wt. % gluconolactone, 4 wt. % glycerin, 5 wt. % glyceryl stearate SE, 0.1 wt. % devil's claw root extract, 0.5 wt. % sunflower seed oil, 0.1 wt. % yerba mate leaf extract, 3 wt. % magnesium sulfate, 0.15 wt. % peppermint oil, 1.25 wt. % menthol, 0.02 wt. % skullcap root extract, 0.3 wt. % sodium benzoate, 2 wt. % sorbitan olivate, 3 wt. % stearic acid, 0.1 wt. % vitamin E, 0.5 wt. % xanthan gum, 0.02 wt. % yucca root extract, and water to make 100%.

7. A method of treating localized pain, inflammation, or swelling in a human subject in need of such treatment which comprises topically applying to the site of the pain, inflammation, or swelling the composition of claim 1.

8. The method of claim 7 wherein the pain is arthritic pain.

9. The method of claim 7 wherein the pain is caused by strenuous exercise.

10. The method of claim 7 wherein the site of the pain, inflammation, or swelling is the arm or shoulder of a baseball pitcher.

11. A method of treating localized pain, inflammation, or swelling in a human subject in need of such treatment which comprises topically applying to the site of the pain, inflammation, or swelling the composition of claim 2.

12. A method of treating localized pain, inflammation, or swelling in a human subject in need of such treatment which comprises topically applying to the site of the pain, inflammation, or swelling the composition of claim 3.

13. A method of decreasing the arm pain and improving the accuracy of a baseball pitcher in a throwing session that comprises applying the composition of claim 1 to the throwing arm and shoulder prior to and/or after the throwing session.

14. A method of decreasing the arm pain and improving the accuracy of a baseball pitcher in a throwing session that comprises applying the composition of claim 2 to the throwing arm and shoulder prior to and/or after the throwing session.

15. A method of decreasing the arm pain and improving the accuracy of a baseball pitcher in a throwing session that comprises applying the composition of claim 3 to the throwing arm and shoulder prior to and/or after the throwing session.

16. A method of preventing or minimizing anticipated localized pain, inflammation, or swelling in a human subject in need of such treatment which comprises topically applying to the site of the anticipated pain, inflammation, or swelling the composition of claim 1.

17. A method of preventing or minimizing anticipated localized pain, inflammation, or swelling in a human subject in need of such treatment which comprises topically applying to the site of the anticipated pain, inflammation, or swelling the composition of claim 2.

18. A method of preventing or minimizing anticipated localized pain, inflammation, or swelling in a human subject in need of such treatment which comprises topically applying to the site of the anticipated pain, inflammation, or swelling the composition of claim 3.

* * * * *